(12) United States Patent
Jenness et al.

(10) Patent No.: US 6,399,825 B1
(45) Date of Patent: Jun. 4, 2002

(54) PROCESS FOR MANUFACTURE OF DIMETHYL ACETAMIDE

(75) Inventors: Tod F. Jenness, Decatur, AL (US); Terry L. Tolliver, St. Louis, MO (US)

(73) Assignee: Solutia Inc., St. Louis, MO (US)

( * ) Notice: Subject to any disclaimer, the term of this patent is extended or adjusted under 35 U.S.C. 154(b) by 0 days.

(21) Appl. No.: 09/585,302

(22) Filed: Jun. 1, 2000

Related U.S. Application Data

(60) Provisional application No. 60/136,997, filed on Jun. 1, 1999.

(51) Int. Cl.[7] .............................................. C07C 231/02
(52) U.S. Cl. ........................ 564/138; 564/133; 564/215
(58) Field of Search ................................ 564/138, 133, 564/215

(56) References Cited

U.S. PATENT DOCUMENTS 3,300,531 A * 1/1967 James, Jr. et al.
3,627,830 A * 12/1971 Horst et al.

FOREIGN PATENT DOCUMENTS

DE          44 32 540 A1    3/1995    ......... C07C/02/233

OTHER PUBLICATIONS

Symes, J. et al, Phosphoryl to carbonyl migration of amino groups in mixed anhydrides, Can J. Chem, 1986, vol. 64, pp. 1702–1708.

* cited by examiner

*Primary Examiner*—Shailendra Kumar
(74) *Attorney, Agent, or Firm*—Howrey Simon Arnold & White, LLP

(57) ABSTRACT

A process for the increasing the conversion of raw materials into DMAc by increasing the temperature at which the reaction occurs. The higher temperature is achieved by installing a pressure control valve in the dimethyl amine recycle line returning to the scrubber column. This raises back pressure on reactor and reactor column. The higher pressure raises the temperature in reactor vessel. Higher temperature increases the reaction rate and efficiency. The implementation of this invention greatly increases the capacity of existing equipment without adding large amounts of capital to expand conventional methods.

21 Claims, 2 Drawing Sheets

PROCESS FOR MANUFACTURE OF DIMETHYL ACETAMIDE

This application claims the benefit of U.S. Provisional Application No. 60/136,997, filed Jun. 1, 1999.

BACKGROUND OF THE INVENTION

This invention is generally related to the manufacture of dimethyl acetamide (DMAc) solvent from the raw materials acetic acid and dimethyl amine and, more particularly, to a process for increasing the conversion of raw materials to dimethyl acetamide by increasing the pressure in the reactor vessel.

Use of dimethyl acetamide as a solvent is expanding since the environmental classification of dimethyl formamide was determined to be carcinogenic. Dimethyl acetamide is used as a solvent for plastics, resins, gums, and electrolytes. It is also used in catalysis, as a paint remover, and as a high purity solvent for crystallization and purification.

DMAc is formed by two reactions starting with dimethylamine (DMA) and acetic acid (HOAc). The first reaction typically occurs in a scrubber column where glacial acetic acid and DMA contact each other in an exothermic reaction to form an intermediate salt, dimethyl ammonium acetate (DMAA). The salt is then broken down to dimethyl acetamide (DMAc) and water with the addition of heat. This reaction is temperature dependent. This second reaction typically occurs in a reactor and a reactor column. DMA is fed to the reactor. Past experience shows that approximately ⅓ of the DMA reacts in the reactor and reactor column, and the remainder passes through a partial condenser as vapor to react in the scrubber. This invention improves conversion so that approximately ⅔ of the DMA reacts in the reactor and reactor column.

Recovered acid is combined with a reactor purge stream and fed to a heels column where the higher boiling monomethyl acetamide (MMAc) is separated from DMAc and HOAc. The concentrated MMAc is removed batch-wise from the heels column sump to a pan dryer. The recovered acid and DMAc are then pumped from the heels column overhead back to the scrubber column where the recovered acid can contact the DMA to form the salt, DMAA.

Attempts to increase conversion in the past have involved different dimethyl amine (DMA) feed locations in the reactor, and different reactor column packing and vapor/liquid distributors. None of these changes affected manufacturing capacity or conversion efficiency. All prior DMAc manufacturing technology uses back pressure on the reactor created by the process equipment and does not make any attempt to control reactor pressure.

Demand for dimethyl acetamide is increasing, and a need exists for lower cost manufacturing processes and equipment.

SUMMARY OF THE INVENTION

The present invention concerns a process for manufacturing dimethyl acetamide, which includes the steps of: reacting acetic acid and dimethyl amine to form an intermediate salt, typically dimethyl ammonium acetate; converting the salt into dimethyl acetamide and water in a reactor; maintaining a substantially constant elevated pressure inside the reactor by using an automated pressure control valve; and separating the dimethyl acetamide, for example from unreacted acetic acid, dimethyl amine, and water. Preferably the pressure in the reactor is between about 2 and 10 pounds per square inch gauge.

The acetic acid fed to the process preferably is glacial acetic acid. It is also preferred that the reaction of the acetic acid and dimethyl amine take place at least partially in a scrubber column. It is further preferred that the pressure control valve be controlled by a feedback loop.

In another embodiment of the invention, the process includes the steps of: reacting acetic acid and dimethyl amine to form an intermediate salt; converting the salt into dimethyl acetamide and water in a reactor; maintaining a substantially constant elevated temperature inside the reactor using an automated pressure control valve; and separating the dimethyl acetamide. Preferably in this embodiment the temperature in the reactor is from 163 to 180° C.

One specific embodiment of the invention is a process for manufacturing dimethyl acetamide, comprising the steps of: reacting acetic acid and dimethyl amine to form dimethyl ammonium acetate; converting the salt into dimethyl acetamide and water in a reactor; maintaining a substantially constant pressure of from about 2–10 psig and a substantially constant temperature of from about 163–180° C. inside the reactor by using an automated pressure control valve; and separating the dimethyl acetamide from water.

The process of the present invention increases the conversion of raw materials into DMAc by increasing the temperature at which the reaction occurs. In one particular embodiment of the process, the higher temperature is achieved by installing a pressure control valve in a dimethyl amine recycle line returning to the scrubber column. This raises back pressure on reactor and reactor column. The higher pressure raises the temperature in reactor vessel. Higher temperature increases the reaction rate and efficiency. The implementation of this invention greatly increases the capacity of existing process equipment without requiring large amounts of capital for additional equipment. Therefore, the present invention allows more economical production of DMAc.

DESCRIPTION OF ILLUSTRATIVE EMBODIMENTS

Figure 1:
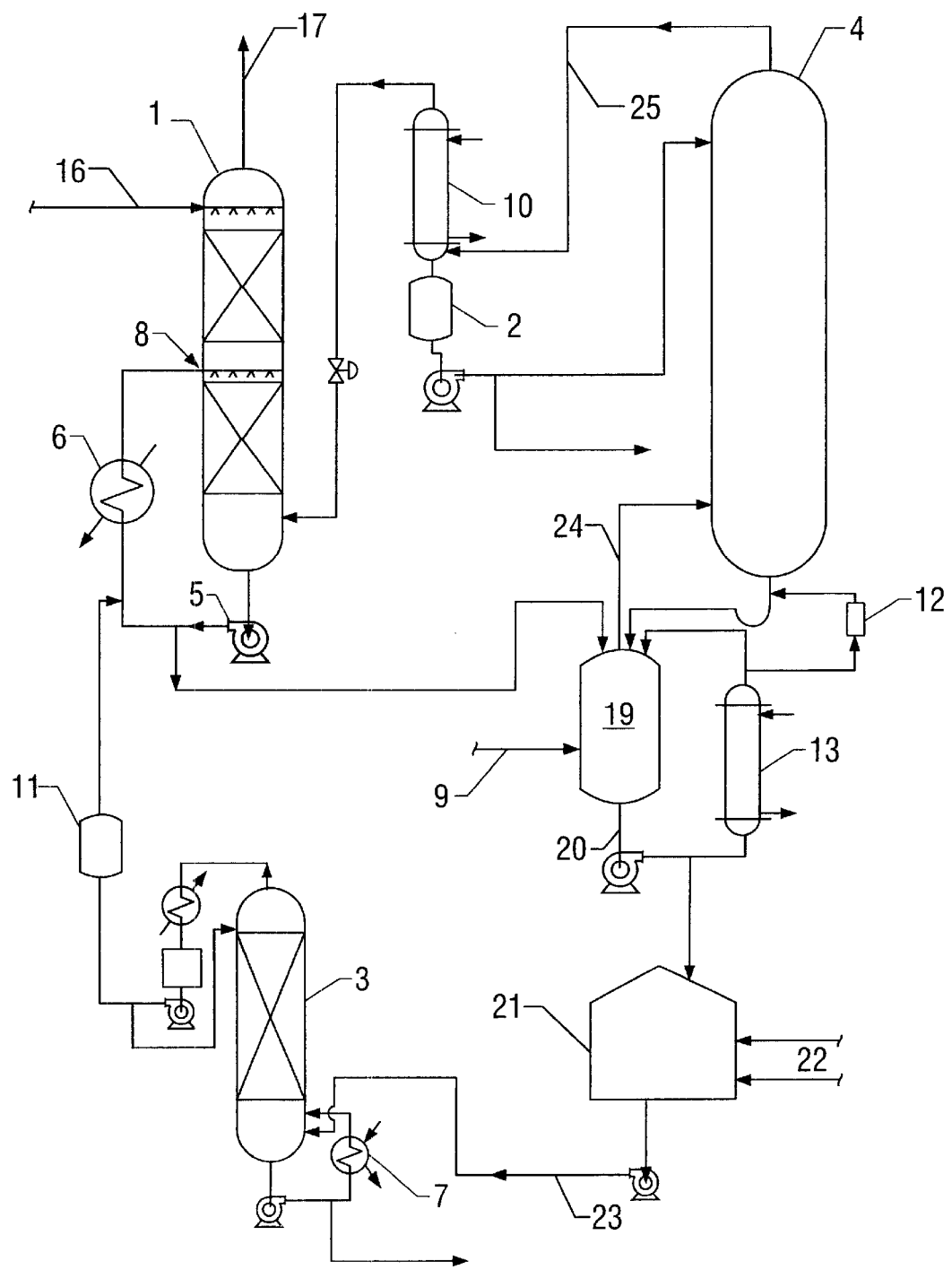
FIG. 1 is a process flow diagram of a dimethyl acetamide manufacturing process that does not employ pressure control for the reactor column.

FIG. 1 shows a conventional system for the production of DMAc that does not employ the pressure control of the present invention. Generally, the basic process starts with glacial acetic acid fed into a scrubber column which contains DMA vapor. The acetic acid and DMA react to form DMAA. DMA is added to the stream of DMAA, and this stream is passed into a series of two reactors where it is converted into DMAc and water. The DMAc is then separated from the water and unreacted materials.

A fresh glacial acetic acid stream (16) and a fresh DMA stream (9) are fed to different points in the process. The acetic acid (16) is fed to a scrubber column (1), which also contains DMA vapor. The acetic acid and DMA react in the column to form DMAA. The overhead (17) from the scrubber column is vented. The scrubber column bottoms stream (18), containing DMAA as well as some unreacted acetic acid and DMA, is partially recycled through a scrubber cooler (6) to the scrubber column (1). The remainder of the scrubber bottoms (18) flow to a vessel (19), to which the fresh DMA (9) is also fed.

The bottoms (20) from the vessel (19) partially flows through a heels column (13), and partially flows to a tank (21). Also fed to the tank (21) are streams (22) from evaporators and acid removal column bottoms, that contain some acetic acid. A stream (23) drawn from this tank is pumped to a reactor vessel (3), in which the temperature is high enough to convert DMAA to DMAc and water. Approximately 65% of the new DMA feed (9) to the reactor (3) leaves unreacted and flows on to the scrubber column (1), where it is largely converted to the salt.

The overhead stream (24) from the vessel (19) flows to a reactor column (4), in which the temperature is sufficiently high to convert DMAA to DMAc and water. A portion of an overhead stream (25) from the reactor column (4) is recycled to the column (4) and another portion of that overhead stream flows through a heat exchanger (10) to the scrubber column (1).

Examples of suitable temperatures and pressures are: 22° C. for the overhead (17) from the scrubber column; 85° C. for the bottoms (18) from the scrubber column; and 40° C. for the reactor column overhead stream (25) after it has passed through the heat exchanger (10).

The scrubber column (1) provides vapor-liquid contact area for the unreacted DMA vapor from the reactor column condenser (2) and the fresh glacial acetic acid. The reaction is exothermic to form an intermediate salt, DMAA. This salt is passed to the reactor (3) and reactor column (4) where it breaks down under heat to form dimethyl acetamide and water.

The pump return (5) from the scrubber cooler (6) can feed into various locations in the column (1) such as near the top of the column, or near the middle of the column. When water is present, the reactor reboiler (7) may not be able to boil up a continuous rate and may tend to slug the reactor column (4) and condenser (2) with vapor. DMA venting is improved by introducing the cooler pump return (5) to the center distributor (8).

One potential problem is that the acetic acid might tend to gel as the scrubber top temperature drops from 65° C. to 25° C. This can be avoided by continuously re-circulating liquid through the top section of packing.

A column differential pressure controller (not shown) sets the amount of new acetic acid fed to column (1). The best vapor-liquid distribution is achieved by directing the return nozzle from the cooler pump return (5) to the middle of the column (1).

The heat exchanger (10) area may not be sufficient to boil any appreciable amount of water. Liquor concentrations above 0.5% water can be enough to lose boil-up capacity. Start-up material collected in the ARB (Acid Removal Bottoms) tank (11) is preferably reclaimed through the reactor (3) and not the scrubber (1) due to the water generated from the reaction.

Iron can be added in the form of #8 nails through the nail pot (12). Originally thought to be a corrosion inhibitor, the iron would actually appear to be a catalyst for the salt decomposition. All feeds being equal, the percent acetic acid in the new solvent was 1.1%, 1.5% 2.0% for iron concentrations of 4000 ppm, 2000 ppm, 1000 ppm.

The reactor column (4) provides liquid hold-up time for the salt to decompose to DMAc and water. As with the heels column (13) and scrubber (1), the packing is made up of commercially available ceramic rings (e.g., one inch rings).

Figure 2:
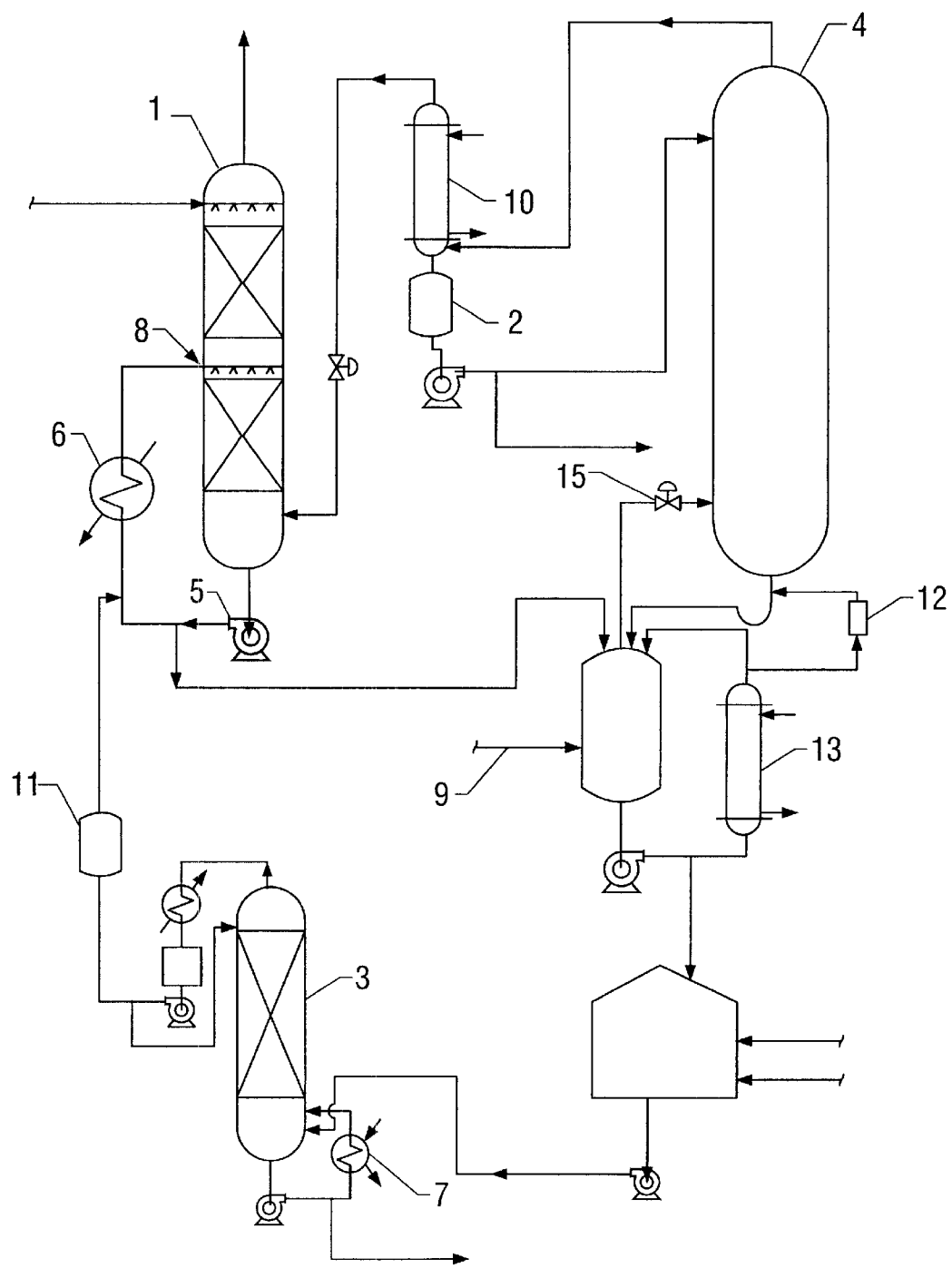
FIG. 2 is a process flow diagram of a dimethyl acetamide manufacturing process of the present invention.

FIG. 2 illustrates one embodiment of the claimed invention. The claimed invention is an improvement over the conventional process shown in FIG. 1. While the basic process is the same, the addition of a pressure control valve for the reactor produces unexpected conversion efficiency. Since some aspects of the conventional process are incorporated in the process of FIG. 2, for brevity, they will not be repeated.

A pressure control valve (15) is located at DMA vapor inlet to the scrubber column (4) to increase pressure and temperature in the reactor and reactor column. Suitable pressure control valves can be, for example, ball valves, gate valves, or other types of valve known to those skilled in the art, available commercially from suppliers such as Fisher-Rosemount.

Preferably the pressure in the reactor column (4) is from about 3.5–6.5 psig, and the pressure in the reactor (3) is from about 4–7 psig. Preferably the overhead temperature of the reactor column (4) is from about 150–170° C., and the overhead temperature of the reactor (3) is from about 163–180° C.

The DMAc formation reaction is temperature sensitive and occurs more rapidly at higher temperatures. Raising reactor column (4) pressure from 0.5 psig to 6 psig increased the temperature of the reacting liquor from 163° C. to 175° C. The pressure preferably is maintained substantially constant, i.e. not more than a 5% variation. As a result of the higher temperature the unit's capacity was increased accompanied by a reduction in unreacted acid in the product. Since it was also determined that the salt decomposition was time dependent, the reactor column preferably utilizes a bubble cap tray design. Bubble cap trays give more liquid hold up time than random packing. Other column designs, including other types of packing, could be used instead.

The foregoing description of the invention has been directed to a particular embodiment for purposes of explanation and illustration. It will be apparent, however, to those skilled in the art that modifications to the apparatus described may be made without departing from the essence of the invention. Such modifications may include, but are not limited to, different packing for the columns, for example using random ceramic packing such as saddles. Those skilled in the art will recognize that various substitutions and modifications may be made to the invention without departing from the scope and spirit of the invention as recited in the appended claims.

What is claimed is:

1. A process for manufacturing dimethyl acetamide, comprising:
   reacting acetic acid and dimethyl amine to form an intermediate salt in a first column;
   converting the salt into dimethyl acetamide and water in a reactor;
   maintaining a substantially constant pressure above 2 psig inside the reactor by using an automated pressure control valve; and
   separating the dimethyl acetamide.

2. A process for manufacturing dimethyl acetamide as in claim 1, where the pressure in the reactor is between about 2 and 10 pounds per square inch gauge.

3. A process for manufacturing dimethyl acetamide as in claim 1, where the automated pressure control valve is a ball valve.

4. A process for manufacturing dimethyl acetamide as in claim 1, where the automated pressure control valve is a globe valve.

5. A process for manufacturing dimethyl acetamide as in claim 1, where the intermediate salt is dimethyl ammonium acetate.

6. A process for manufacturing dimethyl acetamide as in claim 1, where the acetic acid is glacial acetic acid.

7. A process for manufacturing dimethyl acetamide as in claim 1, where the reaction of the acetic acid and dimethyl amine takes place in a scrubber column.

8. A process for manufacturing dimethyl acetamide as in claim 1, where the pressure control valve is controlled by a feedback loop.

9. A process for manufacturing dimethyl acetamide as in claim 1, where the dimethyl acetamide is separated from the acetic acid, dimethyl amine, and water in a heels column.

10. A process for manufacturing dimethyl acetamide as in claim 1, where the automated pressure control valve controls the flow of a stream fed to the reactor.

11. A process for manufacturing dimethyl acetamide, comprising:

reacting acetic acid and dimethyl amine to form an intermediate salt in a first column;

converting the salt into dimethyl acetamide and water in a reactor;

maintaining a substantially constant elevated temperature above 160° C. inside the reactor using an automated pressure control valve; and separating the dimethyl acetamide.

12. A process for manufacturing dimethyl acetamide as in claim 11, where the temperature in the reactor is from 163 to 180° C.

13. A process for manufacturing dimethyl acetamide as in claim 11, where the automated pressure control valve is a ball valve.

14. A process for manufacturing dimethyl acetamide as in claim 11, where the automated pressure control valve is a globe valve.

15. A process for manufacturing dimethyl acetamide as in claim 11, where the intermediate salt is dimethyl ammonium acetate.

16. A process for manufacturing dimethyl acetamide as in claim 11, where the acetic acid is glacial acetic acid.

17. A process for manufacturing dimethyl acetamide as in claim 11, where the reaction of the acetic acid and dimethyl amine takes place in a scrubber column.

18. A process for manufacturing dimethyl acetamide as in claim 11, where the pressure control valve is controlled by a feedback loop.

19. A process for manufacturing dimethyl acetamide as in claim 11, where the dimethyl acetamide is separated from the acetic acid, dimethyl amine, and water in a heels column.

20. A process for manufacturing dimethyl acetamide as in claim 11, where the automated pressure control valve controls the flow of a stream fed to the reactor.

21. A process for manufacturing dimethyl acetamide, comprising:

reacting acetic acid and dimethyl amine to form dimethyl ammonium acetate in a first column;

converting the salt into dimethyl acetamide and water in a reactor;

maintaining a substantially constant pressure of from about 2–10 psig and a substantially constant temperature of from about 170–180° C. inside the reactor by using an automated pressure control valve; and separating the dimethyl acetamide from water.

* * * * *